US008987292B2

(12) United States Patent
Safdi et al.

(10) Patent No.: US 8,987,292 B2
(45) Date of Patent: Mar. 24, 2015

(54) RIFAXIMIN ANTI-RECTAL DYSFUNCTION PREPARATION

(75) Inventors: Alan Safdi, Cincinnati, OH (US); David Taylor, Chapel Hill, NC (US)

(73) Assignee: Salix Pharmaceuticals, Ltd., Raleigh, NC (US)

( * ) Notice: Subject to any disclaimer, the term of this patent is extended or adjusted under 35 U.S.C. 154(b) by 1054 days.

(21) Appl. No.: 12/224,774

(22) PCT Filed: Mar. 6, 2007

(86) PCT No.: PCT/US2007/005846
§ 371 (c)(1),
(2), (4) Date: Nov. 6, 2009

(87) PCT Pub. No.: WO2007/103448
PCT Pub. Date: Sep. 13, 2007

(65) Prior Publication Data
US 2010/0048520 A1 Feb. 25, 2010

Related U.S. Application Data

(60) Provisional application No. 60/781,144, filed on Mar. 9, 2006, provisional application No. 60/791,236, filed on Apr. 11, 2006.

(51) Int. Cl.
  A61K 31/44 (2006.01)
  A61K 31/04 (2006.01)
  A61K 45/06 (2006.01)
  A61K 9/00 (2006.01)
  A61K 9/02 (2006.01)

(52) U.S. Cl.
  CPC ............... *A61K 45/06* (2013.01); *A61K 9/0031* (2013.01); *A61K 9/02* (2013.01)
  USPC .......................................... 514/283; 514/742

(58) Field of Classification Search
  USPC ................................. 514/283, 742
  See application file for complete search history.

(56) References Cited

U.S. PATENT DOCUMENTS

2001/0025057 A1* 9/2001 Gorfine ......................... 514/742
2002/0111334 A1* 8/2002 Ekwuribe et al. ............. 514/150

FOREIGN PATENT DOCUMENTS

WO WO-2001011334 A2 2/2001
WO WO-2006063133 A2 6/2006

OTHER PUBLICATIONS

DuPont HL, Ericsson CD, Mathewson JJ, Palazzini E, DuPont MW, Jiang ZD, Mosavi A, de la Cabada FJ. Rifaximin: a nonabsorbed antimicrobial in the therapy of travelers' diarrhea. Digestion. Nov.-Dec. 1998;59(6):708-14.*

Boschetto S, Giovannone M, Tosoni M, Barberani F. Hydropneumatic anal dilation in conservative treatment of chronic anal fissure: clinical outcomes and randomized comparison with topical nitroglycerin. Tech Coloproctol. Aug. 2004;8(2):89-92.*

Jensen SL. Treatment of first episodes of acute anal fissure: prospective randomised study of lignocaine ointment versus hydrocortisone ointment or warm sitz baths plus bran. Br Med J (Clin Res Ed). May 3, 1986;292(6529):1167-1169.*

Scarpignato C, Pelosini I. Rifaximin, a poorly absorbed antibiotic: pharmacology and clinical potential. Chemotherapy. 2005;51 Suppl 1:36-66.*

Meyers JS, Rubin DT, Ginsburg PM, Ehrenpreis ED. Treatment of anal fissures with topical nitroglycerin. Expert Opin Pharmacother. Jan. 2001;2(1):41-5.*

Altomare, Donato F. et al.: Glyceryl Trinitrate for Chronic Anal Fissure—Healing or Headache? Results of a Multicenter, Randomized, Placebo-controlled, Double-blind Trial; Dis Colon Rectum, 43(2), 2000; pp. 174-179.

Kennedy, M. L., et al.: Glyceryl Trinitrate Ointment for the Treatment of Chronic Anal Fissure; Dis Colon Rectum, 42(8), 1999; pp. 1000-1006.

Lund, Jonathan N., et al.: A randomised, prospective, double-blind, placebo-controlled trial of glyceryl trinitrate ointment in treatment of anal fissure; Lancet 1997; 349: pp. 11-14.

Watson, S. J., et al.: Topical glyceryl trinitrate in the treatment of chronic anal fissure; British Journal of Surgery, 1996; 83, pp. 771-775.

Nelson, R., A Systematic Review of Medical Therapy for Anal Fissure, Dis Colon Rectum, vol. 47;422-431 (2004).

Sinyaku et al., <Japanese Article> [Journal of New Remedies and Clinics], vol. 26; 2153-2154 (1977) [summary].

* cited by examiner

*Primary Examiner* — Paul Zarek
(74) *Attorney, Agent, or Firm* — McCarter & English, LLP; Jonathan M. Sparks; Michael J. DeGrazia

(57) ABSTRACT

The present invention relates to compositions and methods for treating rectal disorders.

29 Claims, No Drawings

RIFAXIMIN ANTI-RECTAL DYSFUNCTION PREPARATION

RELATED APPLICATIONS

This application is a national stage application of PCT/US2007/005846, filed Mar. 6, 2007, which claims the benefit of U.S. Provisional Application Ser. No. 60/781,144, filed Mar. 9, 2006 and to U.S. Provisional Application Ser. No. 60/791,236, filed Apr. 11, 2006. The entire contents of each of the aforementioned applications is hereby incorporated herein by reference.

BACKGROUND

In general, anal disorders, including anal fissure, anal ulcer, and acute hemorrhoidal disease are common, benign conditions of the anal canal, which affect subjects of all ages, races and sexes. However, these conditions can be problematical to treat and inconvenient if not painful to endure. A subject with an anal fissure or ulcer frequently experiences anal pain and bleeding, the pain being more pronounced during and after bowel movements.

Hemorrhoids are specialized vascular areas lying subjacent the anal mucosa. Symptomatic hemorrhoidal disease is manifest by bleeding, thrombosis and/or prolapse of the hemorrhoidal tissues. Commonly, internal hemorrhoidal tissue bulges into the anal canal during defecation causing bleeding and pain. As the tissue enlarges, further bleeding and pain, prolapse and thrombosis can ensue. The thrombosis of hemorrhoids is another cause of bleeding and pain.

The underlying causes of these anal disorders are poorly understood, but these conditions may be associated with infectious agents and infections of the surrounding tissue, wherein the tissue has become contaminated. The case of anal fissure/ulcer, an abnormality contributing to the disease appears to be an as-yet-unidentified problem of the internal anal sphincter muscle. The internal sphincter is a specialized, involuntary muscle arising from the inner circular muscular layer of the rectum. Intra-anal pressure measurements obtained from people suffering from typical anal fissure/ulcer disease show an exaggerated pressure response to a variety of stimuli. The abnormally high intra-anal pressure is generated by the internal sphincter muscle and is responsible for non-healing of the fissure or ulcer and the associated pain.

Various therapies have been devised to treat these anal disorders. Typical, non-surgical therapy includes bulk laxatives and sitz baths. Sitz baths are helpful because they induce relaxation of the anal sphincter mechanism. See e.g., Shafik, "Role of warm-water bath in anorectal conditions: The thermosphincteric reflex, "J. Clin. Gastroenterol., 16:304-308, 1993.

Topical anal therapy is also used in an effort to promote healing, relieve pain, and reduce swelling and inflammation. Many preparations have been tried including those containing local anesthetics, corticosteroids, astringents, and other agents. However, none of these preparations has been shown conclusively to reduce the healing time or to reliably ameliorate associated pain and some of the treatments, such as Neosporin ointment, are very sensitizing. In addition, antibiotics have not been found useful in treating the diseases. There is a need in the art to provide compositions useful to reduce healing times, alleviate pain and promote healing of the affected rectal and anal tissues.

SUMMARY

The present invention is directed to a composition and method for treating anal disorders and diseases such as anal fissure, anal ulcer, haemorrhoidal disease, levator spasm, Crohn's disease, peri and dermatitis, rectal or anal fissures, and skin inflammation, by topical application of the composition to or proximate the affected area.

Described herein are novel rifaximin anti-rectal dysfunction preparations and uses thereof.

In one aspect, provided herein are pharmaceutical preparations comprising an anti-rectal dysfunction agent and rifaximin.

In one embodiment, the anti-rectal dysfunction agent is a nitric oxide modulating agent.

In another embodiment, the antirectal dysfunction agent is one or more of a b-blocker, nitrate, sclerosing agent, acebutolol, alprenolol, amlodipine, arotinolol, atenolol, barnidipine, bepridil, bevantolol, bucumolol, bufetolol, bufuralol, bunitrolol, bupranolol, carazolol, carteolol, celiprolol, cinepazet maleate, diltazem, elgodipine, epanolol, felodipine, gallopamil, imolamine, indenolol, isosorbide dinitrate, isradipine, limaprost, mepindolol, metoprolol, molsidomine, nadolol, nicardipine, nicorandil, nifedipine, nifenalol, nilvadipine, nipradilol, nitroglycerin, oxprenolol, oxyfedrine, ozagrel, penbutolol, pentaerythritol tetranitrate, pindolol, pronethalol, propranolol, ranolazine, semotiadil, sotalol, terodiline, timolol, toliprolol, troinitrate phosphate, verapamil, zatebradine, nomega-nitro-L-arginine methylester (L-NAME), N-monomethyl-L-arginine (L-NMMA), 5-hydroxytryptamine (HT or serotonin) receptor antagonist, alosetron, diltiazem, nifedipine, verapamil, erythritol tetranitrate, isosorbide dinitrate, or pentaerythritol tetranitrate.

In one embodiment, the nitric oxide modulating agent releases nitric oxide under anal disease treatment conditions.

In another embodiment, the anti-rectal dysfunction agent comprises from between about 0.1% to about 10% of the preparation by weight.

In one embodiment, the anti-rectal dysfunction agent comprises from between about 10% to about 50% of the preparation by weight.

In one embodiment, the rifaximin comprises from between about 10% to about 99% of the preparation by weight.

In one embodiment, the rifaximin comprises from between about 25 mg to about 800 mg.

In another embodiment, the rifaximin comprises from between about 100 mg to about 200 mg.

In one embodiment, the composition may further comprise one or more additional therapeutic agents.

In one embodiment, the additional therapeutic agents comprise anti-inflammatory agents, botox, antibiotics, antiviral compounds, anti-neoplastic compounds, anaesthetics, or anti-fungal agents.

In one aspect, provided herein are pharmaceutical preparations comprising from between about 100 to about 200 mg rifaximin and from between about 0.1% and about 2% hydrocortisone.

In one embodiment, the composition may further comprise further comprising from between about 0.01% to about 1% nitro-glycerine.

In one embodiment, he preparation comprises an enema, a foam, an ointment, a paste, or a suppository.

In one aspect, provided herein are methods of treating a subject suffering from an anal disorder comprising administering an effective amount of an anti-rectal dysfunction preparation proximate or to the affected area of the subject.

In another embodiment, the anti-rectal dysfunction preparation comprises rifaximin and an anti-rectal dysfunction agent.

In one embodiment, the affected area comprises one or more of the external anus or distal anal canal of the subject.

In one embodiment, he anal disorder selected from one or more of anal fissure, anal ulcer, acute hemorrhoidal disease, Crohn's disease, irritable bowel syndrome, hemorrhoidal disease, irritable bowel syndrome, inflammatory bowel disease, travelers' diarrhea, large intestinal anal disease, chronic pancreatitis, pancreatic insufficiency or post-surgical disease.

In another embodiment, the antirectal dysfunction agent is a nitric oxide modulating agent.

In another embodiment, he antirectal dysfunction agent is one or more of a b-blocker, nitrate, sclerosing agent, acebutolol, alprenolol, amlodipine, arotinolol, atenolol, barnidipine, bepridil, bevantolol, bucumolol, bufetolol, bufuralol, bunitrolol, bupranolol, carazolol, carteolol, celiprolol, cinepazet maleate, diltazem, elgodipine, epanolol, felodipine, gallopamil, imolamine, indenolol, isosorbide dinitrate, isradipine, limaprost, mepindolol, metoprolol, molsidomine, nadolol, nicardipine, nicorandil, nifedipine, nifenalol, nilvadipine, nipradilol, nitroglycerin, oxprenolol, oxyfedrine, ozagrel, penbutolol, pentaerythritol tetranitrate, pindolol, pronethalol, propranolol, ranolazine, semotiadil, sotalol, terodiline, timolol, toliprolol, troinitrate phosphate, verapamil, zatebradine, nomega-nitro-L-arginine methyl-ester (L-NAME), N-monomethyl-L-arginine (L-NMMA), 5-hydroxytryptamine (HT or serotonin) receptor antagonist, alosetron, diltiazem, nifedipine, verapamil, erythritol tetranitrate, isosorbide dinitrate, or pentaerythritol tetranitrate.

In one embodiment, the nitric oxide modulating agent is capable of releasing nitric oxide under physiological conditions.

In another embodiment, the nitric oxide modulating agent is capable of releasing nitric oxide under anal disease treatment conditions.

In one embodiment, the administering is topical.

In one embodiment, the administering is via a suppository.

In another embodiment, the preparation is applied proximate or to the affected area of the external anus or distal anal canal of the subject.

In one embodiment, the anti-rectal dysfunction agent comprises from between about 0.01% to 10% by weight of the preparation.

In one embodiment, the rifaximin comprises from between about 0.01% to 10% by weight of the preparation.

In one embodiment, the preparation further comprises a carrier.

In another embodiment, the carrier is selected from one or more of white petrolatum, mineral oil, lanolin, distilled water, acetone, and cocoa butter.

In one embodiment, the method may further comprise a corticosteroid.

In one embodiment, the method may further comprise a local anesthetic.

In one embodiment, the composition is formulated as an ointment, a cream, a gel, or a lotion.

In one embodiment, the composition is formulated as a liquid or semisolid.

In another embodiment, the composition is formulated as a suppository.

In one aspect, provided herein are methods of assessing the efficacy of an anal disorder treatment in a subject, monitoring the progress of a subject being treated for an anal disorder, or a method of selecting a subject for treatment of an anal disorder, comprising:
  determining a pre-treatment level of anal disease;
  administering a therapeutically effective amount of one or more of a preparation according to one or more of claims to the subject; and
  determining a post-treatment level of anal disease after an initial period of treatment with the preparation.

In another embodiment, the modulation of the level of anal disease indicates efficacy of the treatment.

In another embodiment, a decrease in anal disease indicates that the treatment is efficacious.

In one embodiment, the modulation of the anal disease is an indication that the subject is likely to have a favorable clinical response to the treatment.

In one embodiment, the composition is formulated for topical use.

Presented herein, according to one aspect, are methods of treating, preventing, or alleviating an anal disorder comprising administering to a subject in need thereof an effective amount of a rifaximin anti-rectal dysfunction preparation.

According to another embodiment, the anal disorder is or is caused by one or more of anal fissure, anal ulcer, and acute hemorrhoidal disease, irritable bowel syndrome, inflammatory bowel disease, (e.g., Crohn's and colitis), travelers' diarrhea, large intestinal anal disease, chronic pancreatitis, pancreatic insufficiency or post-surgical disease (e.g., pouchtis).

Presented herein, according to one aspect, are methods of assessing the efficacy of an anal disorder treatment in a subject, monitoring the progress of a subject being treated for an anal disorder, or a method of selecting a subject for treatment of an anal disorder, comprising:
  determining a pre-treatment level of anal disease;
  administering a therapeutically effective amount of a rifaximin anti-rectal dysfunction preparation to the subject; and
  determining a post-treatment level of anal disease after an initial period of treatment with the rifaximin anti-rectal dysfunction preparation.

In one embodiment, the modulation of the level of anal disease indicates efficacy of the treatment. In one embodiment, it is the symptom improvement which is the measure of the efficacy of treatment, for example, a decrease in pain, decrease in irritation, a decrease in symptoms upon physical examination, e.g., a decrease in swelling, and change in tissue color.

In another embodiment, a decrease in size and/or number of fissures indicates that the treatment is efficacious.

In another embodiment, the modulation of symptoms of anal disease is an indication that the subject is likely to have a favorable clinical response to the treatment.

Presented herein, according to one aspect, are kits for treating an anal disorder in a subject, comprising a rifaximin anti-rectal dysfunction preparation and instructions for use.

Also presented herein, according to one aspect are packaged compositions comprising, a therapeutically effective amount of a rifaximin anti-rectal dysfunction preparation, wherein the preparation is formulated for treating a subject suffering from or susceptible to an anal disorder, and packaged with instructions to treat a subject suffering from or susceptible to an anal disorder.

Other embodiments are disclosed infra.

DETAILED DESCRIPTION

The present invention relates to rifaximin ointment preparations and the uses thereof in the manufacture of medicinal preparations for topical treatment of skin disorders.

As used herein, the term "anal" includes mucosal, muscular and vasculatular tissue of or proximate the anus and/or lower gut. The term "anal disease" or "anal disorder" refer to diseases or disorders of the tissue which may include mucosal, musculature and/or vasculature of or proximate the anus and/or lower gut.

As used herein, an "anti-rectal dysfunction agents," includes "nitric oxide donors," e.g., compounds or mixture of compounds with at least one of such compound(s) which can release nitric oxide under physiological or anal disease treatment conditions.

A "rifaximin anti-rectal dysfunction preparation," as used herein includes ointments, gels, lotions, gel, sol, suspension, spray, mousse, lotion, cream, ointment, paste, slurry, particulate, microparticulate, microsphere, film, slab, wrap, barriers, implants, rectal suppository, rectal cream, rectal ointment, rectal gel, or enema. The pharmaceutical composition can be formulated in a solution, a gel, a foam, an ointment, a cream, a paste, a spray, or the like; or can be formulated as a component of a suppository, a film, a sponge, a condom, a bioadhesive polymer, a diaphragm, or the like. For rectal administration, the pharmaceutical composition can be included in a suppository, ointment, enema, tablet or cream for release of a therapeutic compound into the intestines, sigmoid flexure and/or rectum.

Rifaximin (INN; see The Merck Index, XIII Ed., 8304) is an antibiotic belonging to the rifamycin class of antibiotics, e.g., a pyrido-imidazo rifamycin. Rifaximin exerts its broad antibacterial activity, for example, in the gastrointestinal tract against localized gastrointestinal bacteria that cause infectious diarrhea, irritable bowel syndrome, small intestinal anal disease, Crohn's disease, and/or pancreatic insufficiency. It has been reported that rifaximin is characterized by a negligible systemic absorption, due to its chemical and physical characteristics (Descombe J. J. et al. *Pharmacokinetic study of rifaximin after oral administration in healthy volunteers.* Int J Clin Pharmacol Res, 14 (2), 51-56, (1994)).

Rifaximin is described in U.S. Patent Publication No. 2005/0272754, published on Dec. 8, 2005, which is incorporated herein by reference in their entirety for all purposes. In therapeutic practice, antibiotics may cause bacterial resistance to the same or other similar antibiotics. This is particularly relevant to rifaximin because it belongs to the rifamycin family along with rifampicin, which is the standard of care for the treatment of tuberculosis. The current short course treatment for tuberculosis is a combination therapy involving four active pharmaceutical ingredients: rifampicin, isoniazid, ethambutol and pyrazinamide, with rifampicin playing a pivotal role. Therefore, any drug which jeopardizes the efficacy of the therapy by selecting for resistance to rifampicin would be harmful. (Kremer L. et al. *"Re-emergence of tuberculosis: strategies and treatment,"* Expert Opin. Investig. Drugs, 11 (2), 153-157, (2002)).

Rifaximin is a compound having the structure of formula I:

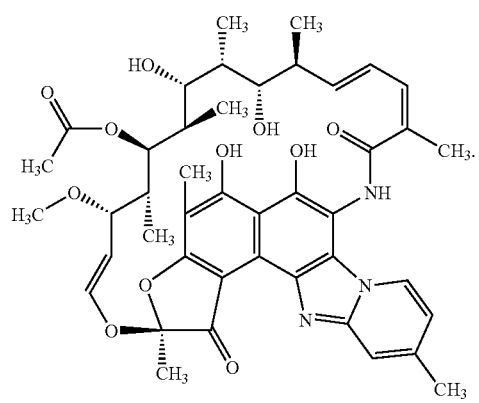

(I)

As used herein, the used to prepare the preparation or in the preparation may be in a polymorphic form or in a amorphous form. Examples of polymomic forms of rifaximin include, for example, polymorph α, polymorph β, polymorph γ, polymorph δ, and polymorph ε of rifaximin, as described in U.S. patent application Ser. No. 10/728,090, U.S. patent application Ser. No. 11/135,651, European Patent Application No. 04005541, Italian Patent Application No. 2003MI2144A1, and European Patent Application No. 15227.

As used herein, the term "about" when used in reference to amounts in formulation, pH, dosages, refers the inherent variability in measurement and designing clinical formulation and dosages. One of skill in the art, having the benefit of this disclosure would understand the use of "about" in these contexts.

Polymorphism, as used herein, refers to the occurrence of different crystalline forms of a single compound in distinct hydrate status, e.g., a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as solubility profiles, melting point temperatures, hygroscopicity, particle shape, density, flowability, compactability and/or x-ray diffraction peaks. The solubility of each polymorph may vary, thus, identifying the existence of pharmaceutical polymorphs is essential for providing pharmaceuticals with predicable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. For a general review of polymorphs and the pharmaceutical applications of polymorphs see G. M. Wall, Pharm Manuf. 3, 33 (1986); J. K. Haleblian and W. McCrone, J. Pharm. Sci., 58, 911 (1969); and J. K. Haleblian, J. Pharm. Sci., 64, 1269 (1975), all of which are incorporated herein by reference.

As used herein, "subject" includes organisms which are capable of suffering from an anal disorder or other disorder treatable by rifaximin or who could otherwise benefit from the administration of a polymorphic compound of the invention, such as human and non-human animals. Preferred human animals include human patients. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. Susceptible to an anal disorder is meant to include subjects at risk of developing an anal disorder infection, i.e., subjects suffering from immune suppression, subjects that have been exposed to another with a bacterial infection, physicians, nurses, subjects traveling to remote areas known to harbor bacteria that causes travelers' diarrhea, etc.

The language "a prophylactically effective amount" of a compound refers to an amount of a compound of the invention of the formula (I) or otherwise described herein which is effective, upon single or multiple dose administration to the patient, in preventing or treating an anal disease.

The language "therapeutically effective amount" of a compound of the invention of the invention refers to an amount of an agent which is effective, upon single or multiple dose administration to the patient, in inhibiting the virus, or in prolonging the survivability of the patient with such an anal disease beyond that expected in the absence of such treatment.

As used herein, "an infection" includes all skin lesions and dermal and mucosal membrane infections.

Rifaximin exerts a broad antibacterial activity in the topically, as well as in the gastrointestinal tract, against localized gastrointestinal bacteria that cause infectious diarrhea, including anaerobic strains. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res,* 14 (2), 51-56, (1994)).

As used herein, anti-rectal dysfunction agents (e.g., nitric oxide modulating agents) include, for example, b-blockers, nitrates, sclerosing agents, including, acebutolol, alprenolol, amlodipine, arotinolol, atenolol, barnidipine, bepridil, bevantolol, bucumolol, bufetolol, bufuralol, bunitrolol, bupranolol, carazolol, carteolol, celiprolol, cinepazet maleate, diltazem, elgodipine, epanolol, felodipine, gallopamil, imolamine, indenolol, isosorbide dinitrate, isradipine, limaprost, mepindolol, metoprolol, molsidomine, nadolol, nicardipine, nicorandil, nifedipine, nifenalol, nilvadipine, nipradilol, nitroglycerin, oxprenolol, oxyfedrine, ozagrel, penbutolol, pentaerythritol tetranitrate, pindolol, pronethalol, propranolol, ranolazine, semotiadil, sotalol, terodiline, timolol, toliprolol, troinitrate phosphate, verapamil, zatebradine, nomega-nitro-L-arginine methylester (L-NAME), N-monomethyl-L-arginine (L-NMMA), or a 5-hydroxytryptamine (HT or serotonin) receptor antagonist, such as ondansetron (24 mg up to every 4-8 hours I.V.; pediatric 0.1 mg/kg/day) or alosetron, diltiazem, nifedipine, verapamil, erythritol tetranitrate, isosorbide dinitrate, or pentaerythritol tetranitrate.

"Nitric oxide modulating agent," as used herein refers to compounds and/or compositions that are capable or adapted to cause or lead to the releases nitric oxide, for example, under anal disease treatment conditions.

Additional therapeutic agents may be included in the rifaximin anti-rectal dysfunction agent. For example, anti-inflammatory agents, steroids, additional antibiotics, antifungal agents, analgesics, or anti-neoplastic agents.

Additional antibiotics may also be desired in the formulation, for example, dapsone, chloramphenicol, neomycin, cefaclor, cefadroxil, cephalexin, cephradine, erythromycin, clindamycin, lincomycin, amoxicillin, ampicillin, bacampicillin, carbenicillin, dicloxacillin, cyclacillin, picloxacillin, hetacillin, methicillin, nafcillin, penicillin, polymyxin, tetracycline, amphotericin-b, candicidin, dermostatin, filipin, fungichromin, hachimycin, hamycin, lucensomycin, mepartricin, natamycin, nystatin, pecilocin, perimycin, azaserine, griseofulvin, oligomycins, neomycin undecylenate, pyrroinitrin, siccanin, tubercidin, viridin, picloxacillin, hetacillin, methicillin, nafcillin, penicillin, polymyxin, or tetracycline.

Organic nitric oxide donors include, for example, at least one organic nitrate, which include esters of nitric acid and may be an acyclic or cyclic compound, such as represented by the following general formula:

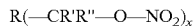

R(—CR'R"—O—NO$_2$)$_x$ wherein:

R is an organic or H (hydro) moiety or covalent bond, preferably a 2 to about 12 carbon hydrocarbon or oxygen-substituted hydrocarbon, especially one having 2 to 6 carbons and from 0 to 2 oxygen(s);

R' is an organic or hydro moiety or covalent bond, and preferably methyl; lower alkyl, to include ethyl, propyl, butyl, pentyl, and hexyl; methoxy; lower alkoxy; or hydro;

R" is an organic or hydro moiety or covalent bond, preferably methyl, lower alkyl, methoxy, lower alkoxy, or hydro, and especially hydro; and x is an integer from 1 to about 12, and preferably from 2 to 6.

For instance, the organic nitrate may be ethylene glycol dinitrate; isopropyl nitrate; glyceryl-1-mononitrate; glyceryl-1,2-dinitrate; glyceryl-1,3-dinitrate; nitroglycerin (GTN); butane-1,2,4-triol-trinitrat-e; erythrityl tetranitrate (ETN); pentaerythrityl tetranitrate (PETN); isosorbide mononitrate (ISMN), which may include isosorbide-2-mononitrate (IS2N) and/or isosorbide-5-mononitrate (ISSN); and/or isosorbide dinitrate (ISDN), and so forth and the like. An advantageous organic nitrate is GTN, and advantageous other organic nitrates include ISDN, ETN, PETN, etc., which may have been given regulatory approval for use in treatments in other fields of medicine on human subjects. In general, the organic nitric oxide donor, to include the organic nitrate, is present in any amount which is effective in the practice of the treatment of anal disease. In typical practice of the invention the organic nitric oxide donor can be present in a concentration from about 0.01 to about 10 percent by weight. All weight percentages herein are based on the total weight of the composition. If GTN is the organic nitrate, preferred concentrations reside in the range of from about 0.01 to about 5 percent by weight. The following table lists some more particular general ranges for other organic nitrates in compositions of the invention: Compound Approximate Weight Percents ISDN 0.01 to 7.5, to include 0.3 to 3 ETN 0.01 to 4, to include 0.1 to 1.5 PETN 0.01 to 4, to include 0.1 to 1.5

Optionally, a corticosteroid may be present in the compositions of the present invention. For instance, the corticosteroid may include hydrocortisone, i.e., 11-17-21-trihydroxypregn-4-ene-3,20-dione or cortisol, cortisol acetate, hydrocortisone phosphate, hydrocortisone 21-sodium succinate, hydrocortisone tebutate, corticosterone, corticosterone acetate, cortisone, cortisone acetate, cortisone 21B-cyclopentanepropionate, cortisone phosphate, triamcinolone hexacetonide, dexamethasone phosphate, desonide, betamethasone dipropionate, mometasone furate, and so forth and the like. In general, the corticosteroid may be present in any amount which is effective in the practice of the treatment of anal disease. In typical practice of the invention, the corticosteroid can be present in a concentration from about 0.001 to about 10 percent by weight and preferably from about 0.1 to about 5 percent by weight. If cortisol is the corticosteroid, preferred concentrations reside in the range of from about 0.5 to about 2.5 percent by weight. If hydrocortisone is the corticosteroid, preferred concentrations reside in the range of from about 0.5 to about 5 percent by weight. If dexamethasone phosphate is the corticosteroid, preferred concentrations reside in the range of from about 0.005 to about 0.03 percent by weight.

The corticosteroid and topical anesthetic may be employed together in the formulations along with rifaximin and an anti-rectal dysfunction agent.

Additional therapeutic agents may also include antifungal agents, for example, allylamines such as butenafine, naftifine, imidazoles such as bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole, triazoles such as fluconazole, itraconazole, saperconazole, terconazole, and others such as acrisorcin, amorolfine, biphenamine, bromosalicylchloranilide, buclosamide, calcium propionate, chlophenesin, ciclopirox, cloxyquin, coparaffinate, diamthazole, dihydrochloride, exalamide, flucytosine, halethazole, hexetidine, loflucarban, nifuratel, potassium iodide, propionates, propionic acid, pyrithione, salicylanilide, sulbentine, tenonitrozole, triacetin, ujothion, undecylenic acid.

Antifungal agents may also include, for example, polyenes such as amphotericin-b, candicidin, dermostatin, filipin, fungichromin, hachimycin, hamycin, lucensomycin, mepartricin, natamycin, nystatin, pecilocin, perimycin, azaserine, griseofulvin, oligomycins, neomycin undecylenate, pyrroinitrin, siccanin, tubercidin, viridin, allylamines such as butenafine, naftifine, imidazoles such as bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole, triazoles such as fluconazole, itraconazole, saperconazole, terconazole, acrisorcin, amorolfine, biphenamine, bromosalicylchloranilide, buclosamide, calcium propionate, chlophenesin, ciclopirox, cloxyquin, coparaffinate, diamthazole, dihydrochloride, exalamide, flucytosine, halethazole, hexetidine, loflucarban, nifuratel, potassium iodide, propionates, propionic acid, pyrithione, salicylanilide, sulbentine, tenonitrozole, triacetin, ujothion, or undecylenic acid.

The other therapeutic agent can include steroid or a non-steroidal anti-inflammatory agent. Useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthatrazone); and alkanones, including nabumetone and pharmaceutically acceptable salts thereof and mixtures thereof. For a more detailed description of the NSAIDs, see Paul A. Insel, Analgesic-Antipyretic and Antiinflammatory Agents and Drugs Employed in the Treatment of Gout, in Goodman & Gilman's The Pharmacological Basis of Therapeutics 617-57 (Perry B. Molinhoff and Raymond W. Ruddon eds., 9$^{th}$ ed 1996) and Glen R. Hanson, Analgesic, Antipyretic and Anti-Inflammatory Drugs in Remington: The Science and Practice of Pharmacy Vol II 1196-1221 (A. R. Gennaro ed. 19th ed. 1995) which are hereby incorporated by reference in their entireties.

For inflammation, preferred treatments for use in combination therapy with the compositions of this invention include (without limitation) naproxen sodium (Anaprox® and Anaprox® DS, Roche), flurbiprofen (Ansaid®; Pharmacia), diclofenac sodium+misoprostil (Arthrotec®, Searle), valdecoxib (Bextra®, Pharmacia), diclofenac potassium (Cataflam® and Voltaren®, Novartis), celecoxib (Celebrex®, Pfizer), sulindac (Clinoril®, Merck), oxaprozin (Daypro®, Pharmacia), salsalate (Disalcid®, 3M), diflunisal (Dolobid®, Merck), naproxen sodium (EC Naprosyn®, Roche), piroxicam (Feldene®, Pfizer), indomethacin (Indocin® and Indocin SR®, Merck), etodolac (Lodine® and Lodine XL®, Wyeth), meloxicam (Mobic®, Boehringer Ingelheim), ibuprofen (Motrin®, Pharmacia), naproxen (Naprelan®, Elan), naproxen (Naprosyn®, Roche), ketoprofen (Orudis® and Oruvail®, Wyeth), nabumetone (Relafen®, SmithKline), tolmetin sodium (Tolectin®, McNeil), choline magnesium trisalicylate (Trilisate®, Purdue Fredrick), and rofecoxib (Vioxx®, Merck).

Antineoplastic agents may also be included in the antirectal dysfunction agents and include for example, vincristine, vinblastine, vindesine, busulfan, chlorambucil, spiroplatin, cisplatin, carboplatin, methotrexate, adriamycin, mitomycin, bleomycin, cytosine arabinoside, arabinosyl adenine, mercaptopurine, mitotane, procarbazine, dactinomycin (antinomycin D), daunorubicin, doxorubicin hydrochloride, taxol, plicamycin, aminoglutethimide, estramustine, flutamide, leuprolide, megestrol acetate, tamoxifen, testolactone, trilostane, amsacrine (m-AMSA), asparaginase (L-asparaginase), etoposide, and interferon a-2a and 2b.

Antivirals agents may also be included in the anti-rectal dysfunction agents and include for example, acyclovir, amantadine, azidothymidine, ribavirin or vidarabine.

In any case where pain in a component of the target disorder, the other therapeutic agent can be an analgesic. Useful analgesics include, but are not limited to, phenacetin, butacetin, acetaminophen, nefopam, acetoamidoquinone, and mixtures thereof.

Optionally, a topical anesthetic may be present in the composition of the invention. For instance, the topical anesthetic may include dibucaine, lidocaine, pramoxine, benzocaine, tetracaine, and so forth and the like. In general, the topical anesthetic may be present in any amount which is effective in the practice of the treatment of anal disease. In typical practice of the invention, the topical anesthetic can be present in a concentration from about 0.1 to about 5 percent by weight and preferably from about 0.5 to about 4 percent by weight based on the total weight of the composition. If dibucaine is the topical anesthetic, preferred concentrations reside in the range of from about 0.25 to about 2 percent by weight. If benzocaine is the topical anesthetic, preferred concentrations reside in the range of from about 10 to about 20 percent by weight. If tetracaine is the topical anesthetic, preferred concentrations reside in the range of from about 1 to about 2 percent by weight.

Pharmaceutical compositions may include, for example, Botox or "*Botulinum* toxin." Botox, as used herein means a neurotoxin produced by *Clostridium botulinum*, as well as a *botulinum* toxin (or the light chain or the heavy chain thereof) made recombinantly by a non-Clostridial species. The phrase "*botulinum* toxin", as used herein, encompasses the *botulinum* toxin serotypes A, B, C, D, E, F and G. *Botulinum* toxin, as used herein, also encompasses both a botulinum toxin complex (i.e. the 300, 600 and 900 kDa complexes) as well as the purified *botulinum* toxin (i.e. about 150 kDa). "Purified *botulinum* toxin" is defined as a *botulinum* toxin that is isolated, or substantially isolated, from other proteins, including proteins that form a *botulinum* toxin complex. A purified *botulinum* toxin may be greater than 95% pure, and preferably is greater than 99% pure. *Botulinum* toxin A, as used herein, refers to *botulinum* toxin type A as further described herein and as known in the art. *Botulinum* toxin B, as used herein, refers to *botulinum* toxin type B as further described herein and as known in the art. *Botulinum* toxin A has been previously described by, for example, Thompson, D. E. et al. (1990) Eur. J. Biochem. 189:73-81 and Binz, T., et al. (1990) J. Biol. Chem. 265:9153-9158. The sequence of *botulinum* toxin A can be found, for example, as Genbank Accession Number Q45894. *Botulinum* toxin B has been previously described by, for example, Whelan, S. M. et al. (1992) Appl.

Environ. Microbiol. 58:2345-2354. The sequence of *botulinum* toxin B can be found, for example, as Genbank Accession Number: P10844.

Methods of Treatment

Provided herein are method of treating, preventing, or alleviating anal disorders comprising administering to a subject in need thereof an effective amount of rifaximin. Anal disorders include one or more of anal fissure, anal ulcer, haemorrhoidal disease, levator spasm, inflammatory bowel disease with anal involvement, irritable bowel syndrome, diarrhea, microbe associated diarrhea, *Clostridium difficile* associated diarrhea, travelers' diarrhea, small intestinal anal disease, Crohn's disease, chronic pancreatitis, pancreatic insufficiency, colitis, hepatic encephalopathy, or pouchitis.

In treatment according to the invention, an amount of active ingredients (e.g., rifaximin and an anti-rectal dysfunction agent) or composition of the invention is contacted with or applied to the affected anal area or proximate thereto such that an effective amount of active ingredient is administered. The amount of active ingredients or composition which is employed should be effective for the amelioration, control and/or healing of the anal disease and the prompt and dramatic control or relief of pain resulting from or associated with the disease. For example, an ointment composition of the invention can be applied topically at each application to the external anus and to the distal anal canal with the finger or an applicator. As an illustrative alternative, the medication can be delivered intra-rectally as a suppository. The medication can be applied in this fashion, for example, three or more times daily in the case of the ointment or once or more times daily in the case of the suppository.

To achieve efficient delivery of a rifaximin anti-rectal dysfunction composition into the skin, one embodiment of the invention includes various formulations of liposomes (phospholipid-based vesicles, cationic liposomes, nonionic liposomes, non ionic/cationic liposomes, pegylated liposomes, PINC polymer, and propylene glycol and ethanol mixture (commonly used vehicle for administering minoxidil), and nonionic liposome/propylene glycol and ethanol mixtures. Reactive liposomes may be preferred for other embodiments of the present invention. Inclusion of cationic amphiphiles as a minor component of liposomes facilitates the association with negatively charged solutes, the rapid binding of liposomes to the cell surface, and the cellular uptake of liposomes. pH-sensitive liposomes have been developed to improve the efficiency of the cytoplasmic delivery of antitumor drugs, proteins, and nucleic acids. Most pH-sensitive liposomes have been prepared using phosphatidylethanolamine (PE). PE alone does not form liposomes and is prone to form the inverted hexagonal phase (HI). However, liposomes can be prepared by adding another bilayer-stabilizing, amphiphilic lipid component to PE. Titratable amphiphiles having a carboxyl group have been used as a component for the preparation of pH-sensitive liposomes. Because the ability to stabilize a bilayer membrane by these titratable amphiphiles decreases under acidic conditions, destabilization results in the fusion of the liposomes. pH-sensitive liposomes are stable at physiological pH, and are internalized by cells through an endocytic pathway, which exposes the liposomes to an acidic pH. Liposomes within the endosome are destabilized and possibly fuse with the endosome membrane, resulting in release of their contents into the cytoplasm without degradation by lysosomal enzymes.

In other embodiments of the invention, sterically stabilized, inert liposomes are particularly suitable. In still other embodiments, targeted liposomes may be used to advantage.

For many applications, mucosal delivery will be used for delivery of rifaximin and anti-rectal dysfunction agents. Mucosal delivery defined here is the local delivery of polyamine effectors to the mucosa of the mouth, GI, and urogenital tract. Mucosally active drugs, can be formulated as either solutions, emulsions or creams, ointments, gels or liposomes using the ingredients described above. In addition, there are also special excipients specifically designed for mucosal delivery. The description, composition, and applicability of these major types of mucosal delivery forms are set forth below. Each is considered suitable for practice of various embodiments of the present invention.

In general, the structure of the mucosal surface is composed of an outermost layer of stratified squamous epithelium, below which lie a basement membrane, a lamina propria followed by the submucosa as the inner-most layer. The mucosae of areas subject to mechanical stress such as the gingivae or the hard palate are also keratinzed, similar to the epidermis. Depending on the keratinition, the mucosa is somewhat permeable. The permeability of oral mucosa is 4-4000 times greater than that of the skin permeability of intestinal mucosa is even greater. The cells of the epithelia are surrounded by an intercellular ground substance, mucous, the principal components of which are complexes of proteins, carbohydrates, lipids and ceramides. Primarily, special mucous-secreting cells, called goblet cells, synthesize mucous. However, in the oral mucosa, most of the mucous is produced by the major and minor salivary glands. Mucous forms a strongly cohesive gel structure that will bind to the epithelial cell surface as a gelatinous layer. The penetration of this mucous layer and the local retention of compound because of its permeability must be achieved for effective mucosal drug delivery. However, this route of administration is very important for the delivery of compounds designed to protect mucosal surfaces from cancer therapy. Since the mucosal surface is a common site in which many of the unwanted side effects occur, the use of formulated mucosally-active drugs designed to prevent these effects is warranted.

Issues to be considered with mucosal delivery are (1) low flux or drug transport through the mucous layer and (2) poor retention and bioadhesion at the mucosal site. Mucosal permeation enhancers are designed to improve drug flux or penetration at the mucosal surface. The use of these enhancers can increase drug permeability by 100-fold or more. Various permeation/absorption enhancers vary in molecular weight and physicochemical properties. In a preferred embodiment for mucosal delivery, permeation enhancers are included in formulations for delivery of a rifaximin anti-rectal dysfunction preparations to the mucosal surface. Most types of enhancers are detergents that include: sodium glycocholate, sodium taurocholate, polysorbate 80, sodium lauryl sulfate, lauric acid, and various alkyl glycosides. Other examples of enhancers include: dextrins (cyclodextrin, dextran sulfate), fatty acids (phosphatidylcholine, lysophosphatidylcholine), heterocyclic compounds (azone), and small molecules (benzalkonium chloride, cetyltrimethylammonium bromide). Each is contemplated for use in the present invention as are other unlisted ingredients typically used for such purpose, as would be appreciated by one of skill in the art The addition of mucoadhesives to the formulation can improve local retention of mucosally delivered compounds. In another preferred embodiment for mucosal delivery, mucoadhesives are included in the polyamine effector formulations of the invention. Mucoadhesive compounds are primarily synthetic or natural polymers that can adhere to the wet mucosal surface. These include synthetic polymers such as monomeric alpha cyanoacrylate, polyacrylic acid, hydroxypropyl methylcellulose, and poly methacrylate derivatives. Glue-like polymers include epoxy resins and polyurethanes. Naturally occurring mucoadhesives include chitosan, hyaluronic acid and xanthan gum. Each is contemplated for use in the present invention as are other unlisted ingredients typically used for such purpose, as would be appreciated by one of skill in the art.

Other delivery vehicles are also suitable for use in the present invention, particularly for administration of polyamine effectors to the mucosa and lumen of the GI and urogenital tract. Nonlimiting examples include: (1) oils such as vegetable oils or fish oils, e.g., olive oil (which can be encapsulated into standard gel capsules); and (2) emulsions prepared, for example, by dispersing polyoxyethylene ethers, e.g., 10-stearyl ether (Brij 76) in aqueous buffer.

Other examples of delivery vehicles suitable for the GI or urogenital mucosa include biodegradable microparticles (preferably in the range of 0.1-10 uM diameter) of polylactic polyglycolic acid, which have been used to deliver proteins to Caco-2 cells as an in vitro model system for gastrointestinal uptake via oral drug delivery (Desai et al., Pharm. Res. 14: 1568-1573, 1997). Significant uptake of proteins carried by polystyrene particles into cells lining the small intestine of the rat has been demonstrated (Hillery et al., J. Drug Targeting 2: 151-156, 1994). Indeed, delivery of protein-containing microparticles has been reported from the GI lumen all the way to the submucosal vasculature (Aphrandan et al., Biol. Cell 61: 69-76, 1987). Therefore, such polymeric microparticles are quite suitable for oral delivery of polyamine effectors to gastrointestinal epithelial cells, which are found on the surface of the GI lumen.

The length of treatment for a particular anal disorder will depend in part on the disorder. For example, rectal fissures may only require treatment duration of 4 times/day to about 6 months, while haemorrhoids may require treatment durations from about 2 times/day for from between about 1 day to about 6 months. Dosages of rifaximin anti-rectal dysfunction preparations will also vary depending on the diseases state. Proper dosage ranges are provided herein infra.

The identification of those patients who are in need of prophylactic treatment for an anal disorder is well within the ability and knowledge of one skilled in the art. Certain of the methods for identification of patients which are at risk of developing an anal disorder which can be treated by the subject method are appreciated in the medical arts, such as personal history, family history, travel history and expected travel plans, the presence of risk factors associated with the development of that disease state in the subject patient. A clinician skilled in the art can readily identify such candidate patients, by the use of, for example, clinical tests, physical examination and medical/family/travel history.

A method of assessing the efficacy of the treatment in a subject includes determining the pre-treatment level of anal disease by methods well known in the art (e.g., observation, examination, patients symptoms, etc.) and then administering a therapeutically effective amount of a rifaximin anti-rectal dysfunction preparation to the subject. After an appropriate period of time (e.g., after an initial period of treatment) after the administration of the preparation, e.g., 2 hours, 4 hours, 8 hours, 12 hours, or 72 hours, the level of anal disease is determined again. The modulation of the bacterial level indicates efficacy of the treatment. The level of anal disease may be determined periodically throughout treatment. For example, the anal disease may be checked every few hours, days or weeks to assess the further efficacy of the treatment. A decrease in anal disease indicates that the treatment is efficacious. The method described may be used to screen or select patients that may benefit from treatment with a rifaximin anti-rectal dysfunction preparation.

In yet another aspect, a method of treating a subject suffering from or susceptible to an anal disorder comprising administering to a subject in need thereof a therapeutically effective amount of a rifaximin anti-rectal dysfunction preparation described herein, to thereby treat the subject. Upon identification of a subject suffering from or susceptible to an anal disorder, for example, rectal fissure, a rifaximin anti-rectal dysfunction preparation is administered.

In one aspect, methods of assessing the efficacy of treatment with a rifaximin anti-rectal dysfunction preparation in a subject comprise determining the pre-treatment level of anal disease, administering a therapeutically effective amount of a rifaximin anti-rectal dysfunction preparation to the subject, and determining the anal disease after an initial period of treatment with the rifaximin anti-rectal dysfunction preparation, wherein the modulation of the anal disease indicates efficacy of a treatment with the rifaximin anti-rectal dysfunction preparation.

Efficacy of a treatment may be measured for example, as reduction of anal disease. Efficacy may also be measured in terms of a reduction of symptoms associated with the anal disorder, a stabilization of symptoms, or a cessation of symptoms associated with an anal disorder, for example, a reduction of bleeding, healing of an anal fissure, decrease in pain associated with the anal disease, a decrease in the number or size of fissures or hemorrhoid, ulceration, tissue infection (dermatitis, (skin infection)), and the like.

In one aspect, methods of monitoring the progress of a subject being treated with a rifaximin polymorph comprise determining the pre-treatment level of anal disease, administering a therapeutically effective amount of a rifaximin polymorph to the subject, and determining the anal disease after an initial period of treatment with a rifaximin polymorph, wherein the modulation of the anal disease indicates efficacy of an anti-viral treatment.

Pharmaceutical Preparations and Formulations

The invention also provides pharmaceutical compositions, comprising an effective amount of rifaximin and a pharmaceutically acceptable carrier. In a further embodiment, the effective amount is effective to treat a bacterial infection, e.g., anal diseases including, one or more of anal fissure, anal ulcer, and acute hemorrhoidal disease, irritable bowel syndrome, travelers' diarrhea, small intestinal anal disease, Crohn's disease, chronic pancreatitis, pancreatic insufficiency, colitis, hepatic encephalopathy, antibiotic associated colitis, and/or diverticular disease.

In a specific embodiment, the pharmaceutical preparation is formulated for topical delivery to skin or hair follicles, and the delivery vehicle comprises an aqueous alcohol mixture and, optionally, propylene glycol. Preparations of this type may be formulated as creams, lotions, ointments or gels. In another specific embodiment, the pharmaceutical preparation is formulated for topical delivery to the oral cavity or nasoesophageal passages. In this embodiment the delivery vehicle preferably comprises a mucoadhesive substance. It may be formulated as an aerosol, oral rinse, ointment or gel. In yet another specific embodiment, the pharmaceutical preparation is formulated for vaginal or rectal delivery and comprises a mucoadhesive substance. These preparations may be formulated as creams, ointments, lotions, gels, foams or suppositories. In still another specific embodiment, the pharmaceutical preparation is formulated for topical delivery to the gastrointestinal tract and the delivery vehicle comprises one or more of nonionic liposomes and mucoadhesive substances.

Preferably, the preparation is formulated as a liquid for coating the surface of the gastrointestinal tract.

When administered in an ointment, gel, foam, spray or the like, our about 0.1 to 2 grams, generally about 0.25 to 0.75 grams, when administered as a suppository or in combination with a solid substrate. An effective amount of a rifaximin anti-rectal dysfunction preparation also can be measured in a weight:weight (w:w) or weight:volume (w:v) amount, for example, about 0.1% to 3% w:w with respect to a solid substrate or about 0.1% to 3% w:v with respect to a pharmaceutically acceptable carrier. In addition, an amount of a rifaximin anti-rectal dysfunction preparation sufficient to reduce, alleviate or cure a rectal disease, can be determined using routine clinical methods, including Phase I, II and III clinical trials.

The invention provides pharmaceutical compositions comprising a rifaximin anti-rectal dysfunction preparation. The pharmaceutical composition further comprises excipients, for example, one or more of a diluting agent, binding agent, lubricating agent, disintegrating agent, coloring agent, flavoring agent or sweetening agent. Composition may be formulated for topical use.

In an embodiment, the a rifaximin anti-rectal dysfunction preparation is administered to the subject using a pharmaceutically-acceptable formulation, e.g., a pharmaceutically-acceptable formulation that provides sustained delivery of the a rifaximin anti-rectal dysfunction preparation to a subject for at least 12 hours, 24 hours, 36 hours, 48 hours, one week, two weeks, three weeks, or four weeks after the pharmaceutically-acceptable formulation is administered to the subject. Examples of extended release devices include, for example, patches.

In certain embodiments, these pharmaceutical compositions are suitable for topical or oral administration to a subject, for example, as a cream, ointment or spray applied to the skin; intravaginally or intrarectally, for example, as a pessary, cream or foam; or aerosol, for example, as an aqueous aerosol, liposomal preparation or solid particles containing the compound.

The phrase "pharmaceutically acceptable" refers to those rifaximin polymorphs of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar, (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The rifaximin anti-rectal dysfunction preparations may conveniently be presented in unit dosage form and may be prepared by any methods well known in the art of pharmacy. The amount of active ingredient (e.g., rifaximin and an anti-rectal dysfunction agent) which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these compositions include the step of bringing into association rifaximin and an anti-rectal dysfunction agent with the carrier and, optionally, one or more accessory ingredients. In general, the formulations are prepared by uniformly and intimately bringing into association the active ingredients with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a rifaximin polymorph(s) as an active ingredient. A compound may also be administered as a bolus, electuary or paste.

The medicinal preparations for topical use may contain rifaximin and an anti-rectal dysfunction agent together with usual excipients, such as white petrolatum, white wax, lanoline and derivatives thereof, stearylic alcohol, propylene glycol, sodium lauryl sulfate, ethers of fatty polyoxyethylene alcohols, esters of fatty polyoxyethylene acids, sorbitan monostearate, glyceryl monostearate, propylene glycol monostearate, polyethylene glycols, methylcellulose, hydroxymethyl propylcellulose, sodium carboxymethylcellulose, colloidal aluminium and magnesium silicate, sodium alginate.

The present invention relates to all of the topical preparations, for instance ointments, pomades, creams, gels and lotions.

When administered in an ointment, gel, foam, spray or the like, our about 0.1 to 2 grams, generally about 0.25 to 0.75 grams, when administered as a suppository or in combination with a solid substrate. An effective amount of a rifaximin anti-rectal dysfunction preparation also can be measured in a weight:weight (w:w) or weight:volume (w:v) amount, for example, about 0.1% to 3% w:w with respect to a solid substrate or about 0.1% to 3% w:v with respect to a pharmaceutically acceptable carrier. In addition, an amount of a rifaximin anti-rectal dysfunction preparation sufficient to reduce, alleviate or cure a rectal disease, can be determined using routine clinical methods, including Phase I, II and III clinical trials.

Suspensions, in addition to the active rifaximin and anti-rectal dysfunction agent, the preparation may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing the rifaximin and the anti-rectal dysfunction agent with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of rifaximin anti-rectal dysfunction agent include powders, sprays, ointments, pastes, creams, lotions, gels, solutions, patches and inhalants. The active rifaximin and anti-rectal dysfunction agent may be mixed under sterile conditions with a pharmaceutically-acceptable carrier, and with any preservatives, buffers, or propellants which may be required.

The ointments, pastes, creams and gels may contain, in addition to rifaximin and anti-rectal dysfunction agent of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to rifaximin and anti-rectal dysfunction agent, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The rifaximin anti-rectal dysfunction agents can be alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of rifaximin anti-rectal dysfunction agents to the body. Such dosage forms can be made by dissolving or dispersing the agent in the proper medium. Absorption enhancers can also be used to increase the flux of the active ingredients across the skin. The rate of such flux can be controlled by either providing a rate controlling membrane or dispersing the active ingredient in a polymer matrix or gel.

Pharmaceutical compositions of the invention suitable for topical administration comprise rifaximin and anti-rectal dysfunction agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various other antibacterial and by antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of rifaximin polymorph(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the rifaximin polymorph(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the rifaximin polymorph(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 100 to 1800 mg per day.

A preferred dose of the rifaximin polymorph for the present invention is the maximum that a patient can tolerate and not develop serious side effects. Preferably, the rifaximin polymorph of the present invention is administered at a concentration of about 1 mg to about 200 mg per kilogram of body weight, about 10—about 100 mg/kg or about 40 mg—about 80 mg/kg of body weight. Ranges intermediate to the above-recited values are also intended to be part of the invention.

In combination therapy treatment, both the compounds of this invention and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment of the invention where another therapeutic agent is administered to an animal, the effective amount of the compound of this invention is less than its effective amount would be where the other therapeutic agent is not administered. In another embodiment, the effective amount of the conventional agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patent visit.

In certain embodiments, one or more compounds of the invention and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the administration of the same compounds of the invention may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than a rifaximin polymorph may be repeated and the administration may be separated by at least at least 1 day, 2 days, 3 days, 5 days, 10 days, 15 days, 30 days, 45 days, 2 months, 75 days, 3 months, or at least 6 months.

Certain indications may require longer treatment times. For example, travelers' diarrhea treatment may only last from between about 12 hours to about 72 hours, while a treatment for Crohn's disease may be from between about 1 day to about 3 months.

Solution-based delivery systems are particularly suitable for the delivery of small organic molecules. In a preferred embodiment of the invention, particularly for administration of a rifaximin anti-rectal dysfunction preparations to the epidermis, alcoholic solutions, as described above, are utilized. An aqueous alcohol-based delivery vehicle has been proven to be highly effective for topical administration of a rifaximin anti-rectal dysfunction preparations. Advantages of this delivery system include, ease of manufacturing, ease of application, fast drying, lack of residue on skin, and ease of analysis of active drug compound after formulation. Solution type formulations are typically administered using dropper bottles or as aerosols.

Emulsions form the basis of cream and lotion-type formulations. Typically, these formulations are colloidal dispersions composed of two immiscible phases; an oil phase and an aqueous phase with an emulsifier. Typical oils used in emulsions include stearyl alcohol, isopropyl lanolate, isopropyl myristate, cetyl alcohol, and vitamin E. Emulsifiers are essentially surfactants that lower the surface tension of the immiscible phases. Most emulsifiers tend to be fatty acid esters or stearates of glycerol, sorbitan, or polyoxyethylene (POE). Depending on the location of the oil and water, emulsions are oil-in-water, water-in-oil or combinations thereof. The preparation of an emulsion commonly requires some mechanical shear force with heat to mix the internal and external phases. Most topical emulsions contain viscosity builders such as natural gums (alginates, carrageenan, tragacanth, pectin, xanthan or collagen) at 1-5% to thicken the preparation. Higher percentages of viscosity builders produce creams, a lower percentage form lotions. Complete formulations for emulsions (creams and lotions) generally include water, alcohol, propylene glycol, sodium lauryl sulfate and white wax. In alternative formulations, they include water, alcohol, glycerol, phosphatidyl choline, lysophosphatidyl choline and triglycerides. For administration of a rifaximin anti-rectal dysfunction preparations to the epidermis, emulsions are particularly well suited. Ease of administration, good local retention and slow release of drug are some of the attractive characteristics of emulsions for a topical delivery system.

Ointments are composed of fluid hydrocarbons meshed in a matrix of higher melting solid hydrocarbons. The hydrocarbon ointment base is typically petrolatum and white ointment Ointments are prepared by melting the base, followed by the addition of excipients, such as antioxidants to the fluid. The drug is then suspended into the ointment by milling. Due to the high oil content, ointments tend to be greasy. Adding components, such as microcrystalline cellulose, which gives the ointment a dry feel on the skin, can reduce greasiness. All ingredients listed above for preparation of ointments are suitable for use in the present invention, as well as unlisted ingredients typically employed for such purpose by one of skill in the art.

Gels are semisolids consisting of a gelling agent that is penetrated with liquid solvent. The concentration and the molecular weight of the gelling agent affect the consistency of vehicle formulation. The gelling agent is a suspension of either large organic or small inorganic molecules. The large organic molecules consisting of either natural or synthetic polymers exist as randomly coiled chains that entangle and form the gel structure. Some common polymers of this kind are natural gums, cellulose derivatives and acrylic acid polymers. Another class of these gels, called thermally sensitive gels, is prepared from poloxamers. In contrast, the small inorganic molecules form the gel structure by forming a somewhat organized three-dimensional network. Common small inorganic polymers include colloidal solids found in silica and clays. The nature of the solvent determines whether the gel is a hydrogel (water-based) or an organogel (non-aqueous solvent based). Gels are attractive topical delivery vehicles for a rifaximin anti-rectal dysfunction preparations because they are relatively easy to prepare and tend to have a long residence time at the site of application allowing the slow release of compound at the desired site. All ingredients listed above for preparation of gels are suitable for use in the present invention, as well as unlisted ingredients typically employed by one skilled in the art for such purpose.

Liposomes are vesicles consisting of amphipathic lipids arranged in one or more concentric bilayers. When lipids are placed in aqueous medium, the hydrophilic interaction of the lipid head groups with water results in the formation of multilamellar and unilamellar systems or vesicles which resemble biological membranes in the form of a spherical shell. Liposomes may be small (0.025-0.05 um) to large multilamellar vesicles (0.05-10 um). Lipids used to prepare the liposomes include phospholipids, sphingolipids, glycosphingolipids, saturated glycerides, steroids (e.g., cholesterol) and synthetic phospholipids. Liposomes are typically prepared by melting the lipid together in aqueous solvent with an emulsifier like POE. The drug is then added and the liposomes are generated through mixing or sonication. The drug is usually entrapped in the vesicle structure. These basic liposomes are sometimes referred to as "conventional liposomes." Several other types of liposomal preparations exist including (1) sterically stabilized liposomes, which are surface coated with an inert hydrophilic polymer, such as polyethylene glycol; (2) targeted liposomes, to which are attached targeting ligands, such as antibodies or fragments thereof, lectins, oligosaccharides or peptides (e.g., choleratoxin B (CTB) is used to target liposomes to the gastrointestinal epithelium); and (3) reactive or "polymorphic" liposomes, which change their phase and structure in response to a particular interaction (this group includes liposomes sensitive to ions (pH, cations), heat and light, among other stimuli.

Liposomes are good vehicles for dermatological applications. Liposomal delivery offers certain advantages over more conventional formulations, including: (1) reduced serious side effects and incompatibility from undesirably high systemic absorption; (2) significantly enhanced accumulation of the delivered substance at the site of administration due to high comparability of liposomes with stratum corneum; (3) ready incorporation of a wide variety of hydrophilic and hydrophobic molecules into the skin; (4) protection of the entrapped compound from metabolic degradation; and (5) close resemblance to the natural membrane structure and their associated biocompatibility and biodegradability. All ingredients listed above and for preparation of various types of liposomes are suitable for use in the present invention, as well as any other such ingredients typically employed by one skilled in the art for such purpose.

Thus, a rifaximin anti-rectal dysfunction preparations are formulated as pharmaceutical preparations for topical or local administration to patients. The following sites of local administration of these pharmaceutical preparations are contemplated: oral, nasal, ophthalmic, gastrointestinal, urogenital and dermal (cutaneous). Selection of a suitable pharmaceutical preparation depends upon the method of administration chosen, and may be made according to protocols well known to medicinal chemists.

The following general composition is used to prepare a suppository dosage form containing rifaximin and an anti-rectal dysfunction agent. This dosage form is used for rectal or vaginal administration for the treatment of rectal disease. The following ingredients are used in the approximate amounts indicated.

100 mg or 200 mg of rifaximin in 30 g cream
1% hydrocordozone
0.2% nitroglycerin
Optionally includes calcium channel blockers (long acting)
In the form of an enema—4× a suppository 800 mg.
Rifaximin 200 mg
Cremophor RH 40 222.0 222.0 222.0
Macrogol 1500 (PhEur)
Macrogol 4000 (PhEur)

Ointments, pastes, creams and gels also can contain excipients, such as starch, tragacanth, cellulose derivatives, silicones, bentonites, silicic acid, and talc, or mixtures thereof. Powders and sprays also can contain excipients such as lactose, talc, silicic acid, aluminium hydroxide, and calcium silicates, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, for instance inert gases such as nitrogen, carbon dioxide, argon or neon.

In one embodiment of the invention, a pharmaceutical formulation is provided as an ointment containing rifaximin and an anti-rectal dysfunction agent as defined herein. The ointment contains approximately 0.01 to 10 wt. %, preferably 0.5 to 8 wt. %, more preferably 4 wt. % to 8 wt. %, and optimally 4 wt. % to 6 wt. %, active agent, which may or may not be in crystalline form. The ointment also contains a skin penetration enhancer or a combination of enhancers for increasing the rate at which the active agent permeates into and/or through the skin or mucosal tissue. Preferably, the enhancer also stabilizes the drug, i.e., renders it less sensitive to heat and/or moisture. The ointment will contain less than about 5 wt. %, preferably less than about 1 wt. %, most preferably less than about 0.5 wt. %, protic solvents that are liquids at temperatures of less than about 30° C., e.g., water, lower alkanols, and the like.

In one embodiment, an ointment contains an enhancer composition comprising at least one component which is a saturated monofunctional or polyfunctional ester which may be either open-chain or cyclic. Such compounds have been found to enhance the stability of the active agent herein. That is, such esters not only result in a formulation which is chemically and physically stable, but, surprisingly, provide a formulation having greater stability than exhibited by the active agent alone. In addition, saturated monofunctional or polyfunctional esters serve as delivery aids with the potential to increase the permeation of the active agent into and/or through the skin or mucosal tissue.

Suitable ester components for incorporation into the enhancer composition are nontoxic organic compounds that are physically and chemically compatible with the active agent and in which the active agent has at least some solubility. Preferred esters are liquid at room temperature and have a molecular weight of less than about 250. Typical esters contain 3-18 carbon atoms and one to three ester functionalities, and are generally lower alkyl esters or cyclic esters. Particularly preferred esters are diethyl succinate, propylene carbonate (PC), diisopropyl adipate (DIA) and triacetin (also known as glyceryl triacetate). In fact, it has been found that these latter four esters work exceptionally well in combinations, to provide optimal enhancement of stability. Generally, the pharmaceutical formulations herein contain on the order of 0.02 wt % to 50 wt. %, preferably on the order of 0.02 wt. % to 20 wt. %, of the enhancer composition. For a formulation containing approximately 6 wt. % active agent, the agent should be at least about 15% (w/w) soluble in the ester component.

In this embodiment, the active agent and enhancer composition are present in an ointment base. As known in the art, ointments are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment base, may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, lanolin and stearic acid. Preferred water-soluble ointment bases are prepared from polyethylene glycols of varying molecular weight; again, reference may be had to Remington: The Science and Practice of Pharmacy for further information. Any of the aforementioned ointment bases may be used herein, although white petrolatum is preferred.

In addition to the active agent, the enhancer composition, and the ointment base, the formulation may contain various additives, known to those skilled in the art. Examples of additives include emulsifiers, solubilizing agents, opacifiers, anti-oxidants, anti-microbial agents, gelling agents, thickening agents, stabilizers, and the like.

Preparation of Ointments Will Employ Techniques of Drug Formulation, particularly topical drug formulation, which are within the skill of the art. Such techniques are fully explained in the literature. See Remington: The Science and Practice of Pharmacy, cited supra, as well as Goodman & Gilman's The Pharmacological Basis of Therapeutics, 9th Ed. (New York: McGraw-Hill, 1996). Generally, the ointment base, e.g., petrolatum or the like, is warmed, combined with all components to be incorporated into the final formulation, and mixed thoroughly. The active agent is typically, although not necessarily, dissolved in the ester penetration enhancer and added last. After sufficient homogeneity has been achieved, the ointment is cooled. It may be desirable to perform the process under an inert atmosphere, e.g., under argon.

Kits

Kits are also provided herein, for example, kits for treating an anal disorder in a subject are provided. The kits may contain, for example, a rifaximin anti-rectal dysfunction preparation and instructions for use. The instructions for use may contain proscribing information, dosage information, storage information, and the like.

Packaged compositions are also provided, and may comprise a therapeutically effective amounts a rifaximin anti-rectal dysfunction preparation and a pharmaceutically acceptable carrier or diluent, wherein the composition is formulated for treating a subject suffering from or susceptible to an anal disorder, and packaged with instructions to treat a subject suffering from or susceptible to an anal disorder.

EXAMPLES

Example 1

Tablet of rifaximin were solubilized in acetone up to 200 mg of rifaximin was added to 30 g of ointment. Nitroglycerin was also added to the ointment.

Example 2

An ointment is prepared by admixing 12.5 g of 2 percent nitroglycerin in white petrolatum, lanolin, and distilled water (nitroglycerin ointment, USP 2%; E. Fougera & Co., Melville, N.Y.) with 37.5 g white petrolatum, USP (VASELINE; Chesebrough-Ponds USA Co., Greenwich, Conn.) and with 100 mg of rifaximin in a laboratory mixing vessel at room temperature.

Example 3

An ointment of 12.5 g of 2 percent nitroglycerin in white petrolatum, lanolin, and distilled water (nitroglycerin ointment, USP 2%; E. Fougera & Co., Melville, N.Y.) is admixed with 20 g of 2.5 percent hydrocortisone in white petrolatum and light mineral oil (hydrocortisone ointment, USP 2.5%; Clay-Park Labs, Inc., Bronx, N.Y.), 100 mg of rifaximin and with 17.5 g of white petrolatum, USP (VASELINE; Chesebrough-Ponds USA Co., Greenwich, Conn.) in a laboratory mixing vessel at room temperature.

Example 4

An ointment of 12.5 g of 2 percent nitroglycerin in white petrolatum, lanolin, and distilled water (nitroglycerin ointment, USP 2%: E. Fougera & Co., Melville, N.Y.) is admixed with 25 g of 1 percent dibucaine, USP, and 200 mg of rifaximin in white petrolatum, light mineral oil, acetone sodium bisulfite, lanolin, and purified water (NUPERCAINAL; Ciba Consumer Pharmaceuticals, Edison, N.J.) and with 12.5 g of white petrolatum, USP (VASELINE; Chesebrough-Ponds USA Co., Greenwich, Conn.) in a laboratory mixing vessel at room temperature.

Example 5

An ointment of 2.5 g of 2 percent nitroglycerin in white petrolatum, lanolin, and distilled water (nitroglycerin ointment, USP 2%; E. Fougera & Co., Melville, N.Y.) is admixed with 20 g of 2.5 percent hydrocortisone, and 200 mg of rifaximin in white petrolatum and light mineral oil (hydrocortisone ointment, USP 2.5%; Clay-Park Labs, Inc., Bronx, N.Y.) and with 25 g of 1 percent dibucaine, USP, in white petrolatum, light mineral oil, acetone sodium bisulfite, lanolin, and purified water (NUPERCAINAL; Ciba Consumer Pharmaceuticals, Edison, N.J.) and with 2.5 g of white petrolatum, USP (VASELINE; Chesebrough-Ponds USA Co., Greenwich, Conn.) in a laboratory mixing vessel at room temperature.

Example 6

An ointment is prepared by admixing 8.75 g of 2 percent nitroglycerin in white petrolatum, lanolin, and distilled water (nitroglycerin ointment, USP 2%; E. Fougera & Co., Melville, N.Y.) with 41.25 g white petrolatum, USP (VASELINE; Chesebrough-Ponds USA Co., Greenwich, Conn.) and 100 mg of rifaximin in a laboratory mixing vessel at room temperature.

The ointment is effective in the treatment of anal disease when applied topically to or proximate the affected area. Therewith, pain relief and healing are significant, and side effects such as headache are few and/or mild. The ointment can be employed with humans.

Example 7

Rifaximin Ointment

Crush rifaximin tablet and dissolve in 0.5 mL of olive oil. Place the mixture through an ointment mill 3 times with a Vaseline™ base. The cream comes out in a pale color.

200 mg of rifaximin in 30 g but or 100 mg rifaximin in 30 g was used.

Alternately, a rifaximin powder may be used.

Example 8

A 77-year-old female presented with recurrent rectal pain. She was found to have a fissure with surrounding inflammation. Her past medical history included recurrent fissures, colonic polyps, diverticulosis, hemorrhoidectomy, and a deep tear during labor and delivery. She had significant disruption of the internal anal sphincter. Surgery was suggested but was not done because of the heightened chance of rectal incontinence. She was initially treated with nitroglycerin cream 0.2% three times a day plus after bowel movements. Stool softeners, sitz baths, and high fiber diet were also recommended. Since the inflammation did not respond she was started on rifaximin ointment (200 mg in 30 g of Vaseline base). She was instructed to use it 3 times a day and with every bowel movement along with other therapy. Patient was seen 4 weeks later and all pain, inflammation, and discomfort resolved. She has not had a recurrence since rifaximin ointment treatment.

Example 9

A 49-year-old healthy male with normal height and weight presented with severe fissures. The patient had a past medical of reflux. Stool softeners, Sitz baths, Tucks pads, and high fiber diet were recommended. Over an 18 month period the fissures were treated with nitroglycerin 0.2%, Analpram HC 1% and 2%, AnaMantle HC, and neomycin plus hydrocortisone suppositories. The patient also treated himself Neosporin plus nitroglycerin without direction from his physician. Treatment with Analpram HC, AnaMantle HC, neomycin plus hydrocortisone suppositories, and Neosporin plus nitroglycerin was unsuccessful. The patient continued treatment with nitroglycerin 0.2% because he had some relief as well as stool softeners, sitz baths, Tucks pads, and high fiber diet. After 18 months the patient (50 years old) was found to have a deep posterior fissure with surrounding inflammation and irritation that was going into the muscle. Rifaximin 100 mg in 30 g Vaseline base 3 times a day and with each bowel movement was added to the current therapy. He was treated for 4 months before there were signs of healing. The patient experienced 3 recurrences over time. Each time he was treated with rifaximin.

Example 10

A 50-year-old male truck driver with chronic fissures for 4-5 years presented with a non-healing fissure. He was previously treated with Botox and underwent surgery. Six months post-surgery he presented with a non-healing fissure. He was started on nitroglycerin 0.2%, sitz baths twice daily. Preparation H pads, Colace twice daily, fiber supplement twice daily, and rifaximin 100 mg in 30 g Vaseline base. The patient used the rifaximin ointment 2 times daily. He complained of stinging when applying the rifaximin ointment; however it resolved after 2 weeks. The patient presented 3 months later healed. No further follow-up is available on this patient.

What is claimed is:

1. A pharmaceutical preparation comprising nitroglycerin and rifaximin.

2. The pharmaceutical preparation of claim 1, wherein the nitroglycerin comprises from between about 0.1% to about 10% of the preparation by weight.

3. The pharmaceutical preparation of claim 1, wherein the nitroglycerin comprises from between about 10% to about 50% of the preparation by weight.

4. The pharmaceutical preparation of claim 1, wherein the rifaximin comprises from between about 10% to about 99% of the preparation by weight.

5. The pharmaceutical preparation of claim 1, wherein the rifaximin comprises from between about 25 mg to about 800 mg.

6. The pharmaceutical preparation of claim 1, wherein the rifaximin comprises from between about 100 mg to about 200 mg.

7. The pharmaceutical preparation of claim 1, further comprising at least one additional therapeutic agents.

8. The pharmaceutical preparation of claim 7, wherein the at least one additional therapeutic agents is selected from the group consisting of: anti-inflammatory agents, botox, antibiotics, antiviral compounds, anti-neoplastic compounds, anaesthetics, or anti-fungal agents.

9. A pharmaceutical preparation comprising from between about 100 to about 200 mg rifaximin and from between about 0.1% and about 2% hydrocortisone.

10. The pharmaceutical preparation of claim 9, further comprising from between about 0.01% to about 1% nitroglycerine.

11. The pharmaceutical preparation of claim 1, wherein the preparation comprises an enema, a foam, an ointment, a paste, or a suppository.

12. A method of treating a subject suffering from an anal disorder comprising administering an effective amount of an nitroglycerin and rifaximin proximal or to an affected area of the subject.

13. The method of claim 12, wherein the affected area comprises one or more of the external anus or distal anal canal of the subject.

14. The method of claim 12, wherein the anal disorder selected from one or more of anal fissure, anal ulcer, acute hemorrhoidal disease, Crohn's disease, irritable bowel syndrome, hemorrhoidal disease, irritable bowel syndrome, inflammatory bowel disease, travelers' diarrhea, large intestinal anal disease, chronic pancreatitis, pancreatic insufficiency or post-surgical disease.

15. The method of claim 12, wherein the administering is topical.

16. The method of claim 12, wherein the administering is via a suppository.

17. The method of claim 12, wherein the preparation is applied proximal or to the affected area of the external anus or distal anal canal of the subject.

18. The method of claim 12, wherein the nitroglycerin comprises from between about 0.01% to 10% by weight of the preparation.

19. The method of claim 12, wherein the rifaximin comprises from between about 0.01% to 10% by weight of the preparation.

20. The method of claim 12, wherein the preparation further comprises a carrier.

21. The method of claim 20, wherein the carrier is selected from one or more of white petrolatum, mineral oil, lanolin, distilled water, acetone, and cocoa butter.

22. The method of claim 12, further comprising a corticosteroid.

23. The method of claim 12, further comprising a local anesthetic.

24. The method of claim 12, wherein the composition is formulated as an ointment, a cream, a gel, or a lotion.

25. The method of claim 12, wherein the composition is formulated as a liquid or semisolid.

26. The method of claim 12, wherein the composition is formulated as a suppository.

27. A method of assessing the efficacy of an anal disorder treatment in a subject, monitoring the progress of a subject being treated for an anal disorder, or selecting a subject for treatment of an anal disorder, comprising:
   determining a pre-treatment level of anal disease;
   administering a therapeutically effective amount of preparation according to claim 1 to the subject; and
   determining a post-treatment level of anal disease after an initial period of treatment with the preparation.

28. The method of claim 27, wherein the modulation of the level of anal disease indicates efficacy of the treatment.

29. The method of claim 27, wherein a decrease in anal disease indicates that the treatment is efficacious.

* * * * *

UNITED STATES PATENT AND TRADEMARK OFFICE
CERTIFICATE OF CORRECTION

PATENT NO. : 8,987,292 B2  
APPLICATION NO. : 12/224774  
DATED : March 24, 2015  
INVENTOR(S) : Alan Safdi et al.

Page 1 of 1

It is certified that error appears in the above-identified patent and that said Letters Patent is hereby corrected as shown below:

In the Claims

In claim 7 (column 26, line 56), replace "agents" with --agent--.
In claim 8 (column 26, line 58), replace "agents" with --agent--.
In claim 10 (column 26, line 67), replace "nitroglycerine" with --nitroglycerin--.
In claim 12 (column 27, lines 5-6), replace "an nitroglycerin" with --nitroglycerin--.
In claim 14 (column 27, lines 11-12), replace "disorder selected" with --disorder is selected--.
In claim 27 (column 28, lines 21-22), replace "of preparation" with --of a preparation--.
In claim 28 (column 28, line 25), replace "the modulation" with --modulation--.

Signed and Sealed this
Eighth Day of September, 2015

Michelle K. Lee
*Director of the United States Patent and Trademark Office*